United States Patent
Simanzhenkov et al.

(10) Patent No.: US 12,240,806 B2
(45) Date of Patent: Mar. 4, 2025

(54) MITIGATING NATURALLY OCCURRING RADIOACTIVE MATERIAL IN OXIDATIVE DEHYDROGENATION

(71) Applicant: NOVA CHEMICALS (INTERNATIONAL) S.A., Fribourg (CH)

(72) Inventors: Vasily Simanzhenkov, Calgary (CA); Bolaji Olayiwola, Calgary (CA); Shahin Goodarznia, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 220 days.

(21) Appl. No.: 18/009,398

(22) PCT Filed: Jun. 8, 2021

(86) PCT No.: PCT/IB2021/055038
§ 371 (c)(1),
(2) Date: Dec. 9, 2022

(87) PCT Pub. No.: WO2021/250568
PCT Pub. Date: Dec. 16, 2021

(65) Prior Publication Data
US 2023/0257326 A1    Aug. 17, 2023

Related U.S. Application Data

(60) Provisional application No. 63/037,760, filed on Jun. 11, 2020.

(51) Int. Cl.
*C07C 5/48* (2006.01)
*B01D 53/02* (2006.01)
(Continued)

(52) U.S. Cl.
CPC ............... *C07C 5/48* (2013.01); *B01D 53/02* (2013.01); *B01D 53/1437* (2013.01);
(Continued)

(58) Field of Classification Search
CPC .... C07C 5/48; C07C 7/11; C07C 7/12; B01D 53/02; B01D 53/1437; B01D 2252/103;
(Continued)

(56) References Cited

U.S. PATENT DOCUMENTS

| 3,501,923 | A | | 3/1970 | Lehmer | |
| 3,904,703 | A | * | 9/1975 | Lo | C07C 5/3332 585/629 |

(Continued)

OTHER PUBLICATIONS

International Search Report and Written Opinion in International Appln. No. PCT/IB2021/055038, mailed on Sep. 3, 2021, 10 pages.

*Primary Examiner* — Prem C Singh
*Assistant Examiner* — Francis C Campanell
(74) *Attorney, Agent, or Firm* — Fish & Richardson P.C.

(57) ABSTRACT

A system for mitigating naturally occurring radioactive materials (NORM) in an oxidative dehydrogenation process includes a feed stream, an oxidative dehydrogenation (ODH) reactor, an effluent stream, a processing unit, and a NORM reduction unit. The feed stream includes oxygen, a hydrocarbon, and NORM. The ODH reactor is configured to receive the feed stream and react the hydrocarbon with the oxygen to form a dehydrogenated hydrocarbon and water. The effluent stream includes the dehydrogenated hydrocarbon, water, unreacted hydrocarbon, and NORM. The processing unit is configured to process the effluent stream to form a product stream and a recycle stream. The product stream includes the dehydrogenated hydrocarbon. The recycle stream includes unreacted hydrocarbon and NORM. The NORM reduction unit is configured to reduce an amount of the NORM in the recycle stream to produce a (Continued)

NORM-reduced recycle stream. The ODH reactor is configured to receive the NORM-reduced recycle stream.

20 Claims, 9 Drawing Sheets

(51) Int. Cl.
    *B01D 53/14*     (2006.01)
    *B01J 19/24*     (2006.01)
    *C07C 7/11*     (2006.01)
    *C07C 7/12*     (2006.01)

(52) U.S. Cl.
CPC .............. *B01J 19/245* (2013.01); *C07C 7/11* (2013.01); *C07C 7/12* (2013.01); *B01D 2252/103* (2013.01); *B01D 2252/205* (2013.01); *B01D 2253/102* (2013.01); *B01D 2253/108* (2013.01); *B01D 2253/1122* (2013.01); *B01D 2253/25* (2013.01); *B01D 2257/93* (2013.01); *B01J 2219/0004* (2013.01)

(58) Field of Classification Search
CPC ........ B01D 2252/205; B01D 2253/102; B01D 2253/108; B01D 2253/1122; B01D 2253/25; B01D 2257/93; B01J 19/245; B01J 2219/0004
USPC .......................................................... 585/324
See application file for complete search history.

(56) References Cited

U.S. PATENT DOCUMENTS

| | | | | |
|---|---|---|---|---|
| 4,120,781 | A | * | 10/1978 | Sie ................. C10G 25/003 |
| | | | | 976/DIG. 383 |
| 6,383,981 | B1 | * | 5/2002 | Blankenship ........ B01J 20/0229 |
| | | | | 502/410 |
| 2009/0318743 | A1 | | 12/2009 | Arnold et al. |

* cited by examiner

MITIGATING NATURALLY OCCURRING RADIOACTIVE MATERIAL IN OXIDATIVE DEHYDROGENATION

CROSS-REFERENCE TO RELATED APPLICATION

This application is a National Stage Application under 35 U.S.C. § 371 and claims the benefit of International Application No. PCT/IB2021/055038, filed Jun. 8, 2021, which claims priority to U.S. Ser. No. 63/037,760, filed on Jun. 11, 2020. The disclosure of the prior applications is considered part of and is incorporated by reference in the disclosure of this application.

TECHNICAL FIELD

This disclosure relates to mitigating naturally occurring radioactive material in oxidative dehydrogenation.

BACKGROUND ART

Naturally occurring radioactive materials (NORM) are radioactive materials that are naturally occurring in low concentrations in the Earth's crust. These materials are the radioactive decay products of radioisotopes such as uranium and thorium and may include materials such as radium-226 and radium-228. During the production of hydrocarbons, these materials may be brought to the surface, often as sulfates, at which point they may precipitate out of solution. One of the decay products from radium is the radon. Radon is a gas that is carried with gas and hydrocarbon flows in pipelines until it further decays to form solid materials, such as lead-210. The solid materials then fall out of the gas or oil stream, forming dust or sludge that mixes with other corrosion products. Over time, these materials may build up in pipelines and other equipment, creating inhalation hazards during cleaning and servicing operations.

SUMMARY OF INVENTION

Certain aspects of the subject matter can be implemented as a system for mitigating naturally occurring radioactive materials (NORM) in an oxidative dehydrogenation process. The system includes a feed stream, an oxidative dehydrogenation (ODH) reactor, an effluent stream from the ODH reactor, a processing unit, and a NORM reduction unit. The feed stream includes oxygen, a hydrocarbon, and NORM. The ODH reactor is configured to receive the feed stream and react at least a portion of the hydrocarbon with the oxygen to form a dehydrogenated hydrocarbon and water. The effluent stream includes the dehydrogenated hydrocarbon, water, a remaining unreacted portion of the hydrocarbon, and the NORM. The processing unit is configured to process the effluent stream to form a product stream and a recycle stream. The product stream includes the dehydrogenated hydrocarbon. The recycle stream includes a remaining portion of the hydrocarbon and the NORM. The NORM reduction unit is configured to reduce an amount of the NORM in the recycle stream to produce a NORM-reduced recycle stream. The ODH reactor is configured to receive the NORM-reduced recycle stream.

This, and other aspects, can include one or more of the following features.

In some embodiments, the NORM reduction unit includes a first adsorption bed. In some embodiments, the system includes a second adsorption bed positioned upstream of the ODH reactor. In some embodiments, the second adsorption bed is configured to remove the NORM from any fluid entering the ODH reactor.

In some embodiments, the system includes a filter positioned upstream of the ODH reactor. In some embodiments, the filter is configured to capture and prevent solid material from entering the ODH reactor.

In some embodiments, the system includes an absorber positioned upstream of the ODH reactor. In some embodiments, the absorber is configured to remove the NORM from the feed stream before the feed stream enters the ODH reactor.

In some embodiments, the system includes a solid material receptacle positioned upstream of the ODH reactor. In some embodiments, the solid material receptacle is configured to accumulate solid material entrained in any fluid entering the ODH reactor.

In some embodiments, the ODH reactor defines an inlet opening coupled to an inlet pipe. In some embodiments, a portion of the inlet pipe is positioned below the inlet opening with respect to gravity. In some embodiments, the solid material receptacle is coupled to the portion of the inlet pipe that is positioned below the inlet opening.

In some embodiments, the inlet pipe includes a baffle configured to direct the solid material to the solid material receptacle.

Certain aspects of the subject matter can be implemented as a system for mitigating NORM in an oxidative dehydrogenation process. The system includes a feed stream, an ODH reactor, an effluent stream form the ODH reactor, a processing unit, and a storage tank. The feed stream includes oxygen, a hydrocarbon, and NORM. The ODH reactor is configured to receive the feed stream and react at least a portion of the hydrocarbon with the oxygen to form a dehydrogenated hydrocarbon and water. The effluent stream includes the dehydrogenated hydrocarbon, water, a remaining unreacted portion of the hydrocarbon, and the NORM. The processing unit is configured to process the effluent stream to form a product stream and a recycle stream. The product stream includes the dehydrogenated hydrocarbon. The recycle stream includes the remaining unreacted portion of the hydrocarbon and the NORM. The storage tank is configured to store the recycle stream for a sufficient time period such that the NORM decays into a solid material. The storage tank is fluidically coupled to the ODH reactor to recycle the remaining portion of the hydrocarbon from the recycle stream to the ODH reactor while the solid material remains within the storage tank.

This, and other aspects, can include one or more of the following features.

In some embodiments, the storage tank includes an outlet configured to discharge the remaining unreacted portion of the hydrocarbon from the recycle stream. In some embodiments, the outlet includes a filter configured to capture and prevent solid material from exiting the storage tank.

In some embodiments, the system includes an adsorption bed positioned upstream of the ODH reactor. In some embodiments, the adsorption bed is configured to remove the NORM from any fluid entering the ODH reactor.

In some embodiments, the system includes a second filter positioned upstream of the ODH reactor. In some embodiments, the second filter is configured to capture and prevent solid material from entering the ODH reactor.

In some embodiments, the system includes an absorber positioned upstream of the ODH reactor. In some embodiments, the absorber is configured to remove the NORM from the feed stream before the feed stream enters the ODH reactor.

In some embodiments, the system includes a solid material receptacle positioned upstream of the ODH reactor. In some embodiments, the solid material receptacle is configured to accumulate solid material entrained in any fluid entering the ODH reactor.

In some embodiments, the ODH reactor defines an inlet opening coupled to an inlet pipe. In some embodiments, a portion of the inlet pipe is positioned below the inlet opening with respect to gravity. In some embodiments, the solid material receptacle is coupled to the portion of the inlet pipe that is positioned below the inlet opening.

In some embodiments, the inlet pipe includes a baffle configured to direct the solid material to the solid material receptacle.

Certain aspects of the subject matter can be implemented as a method to mitigate NORM in an oxidative dehydrogenation process. A feed stream is flowed to an ODH reactor. The feed stream includes oxygen, a hydrocarbon, and NORM. At least a portion of the hydrocarbon is reacted with the oxygen in the ODH reactor to form a dehydrogenated hydrocarbon and water. An effluent stream is discharged from the ODH reactor. The effluent stream includes the dehydrogenated hydrocarbon, water, a remaining portion of the hydrocarbon, and the NORM. The effluent stream is processed to form a product stream and a recycle stream. The product stream includes the dehydrogenated hydrocarbon. The recycle stream include the remaining portion of the hydrocarbon with less NORM than the feed stream. The recycle stream is flowed to the ODH reactor.

This, and other aspects, can include one or more of the following features.

In some embodiments, processing the effluent stream includes separating the remaining portion of the hydrocarbon from a remainder of the effluent stream to form an intermediate stream. In some embodiments, processing the effluent stream includes flowing the intermediate stream through an adsorption bed. In some embodiments, the adsorption bed removes NORM from the intermediate stream to form the recycle stream.

In some embodiments, the feed stream is flowed through a second adsorption bed before the feed stream is flowed to the ODH reactor. In some embodiments, the second adsorption bed removes NORM from the feed stream.

In some embodiments, processing the effluent stream includes separating the remaining portion of the hydrocarbon from a remainder of the effluent stream to form an intermediate stream. In some embodiments, processing the effluent stream includes storing the intermediate stream in a storage tank for a sufficient time period such that the NORM decays into a solid material. In some embodiments, processing the effluent stream includes filtering an outlet stream from the storage tank to remove solid material from the outlet stream, thereby forming the recycle stream.

In some embodiments, the feed stream is filtered to remove solid material from the feed stream before the feed stream is flowed to the ODH reactor.

The details of the implementations of the subject matter of this disclosure are set forth in the accompanying drawings and the description. Other features, aspects, and advantages of the subject matter will become apparent from the description, the drawings, and the claims.

DESCRIPTION OF EMBODIMENTS

This disclosure describes mitigation of naturally occurring radioactive material (NORM) in oxidative dehydrogenation processes. An example of NORM is radon. Additional examples of NORM include decay products, for example, decay products of radon, such as polonium-218, lead-214, bismuth 214, polonium-214, lead-210, bismuth-210, polonium-210, and lead-206. As lead-210 is the longest lived isotope, it is going to be in the highest concentrations in the solids, for example, in the form of dust. NORM can be a contaminant in certain feedstocks for petrochemical plants, refineries, and gas separation plants. Although solid NORM (that is, NORM in solid phase) can typically be removed in various gas and liquids processing equipment, gaseous NORM (that is, NORM in gas phase, for example, radon gas) can distribute into hydrocarbon gas streams, such as ethane and propane streams. If such gaseous NORM is not removed from a process, equipment in the process can potentially be contaminated with radioactive fouling material originating from the gaseous NORM. Equipment that is contaminated with NORM needs to either be decontaminated or disposed as radioactive waste, both of which can be costly and time consuming. If NORM contamination is not dealt with in a timely manner, high radioactivity levels can lead to dangerous incidents. The subject matter described in this disclosure can be implemented in particular embodiments, so as to realize one or more of the following advantages. NORM can be mitigated from the oxidative dehydrogenation process, so that process equipment is protected from being contaminated with radioactive fouling material. This is especially important in processes that do not produce a C3 hydrocarbon stream, as radon accumulates within the process. Further, NORM can be mitigated from the oxidative dehydrogenation process without requiring constant radiation monitoring of an entire facility, which can be a costly exercise.

Figure 1A:
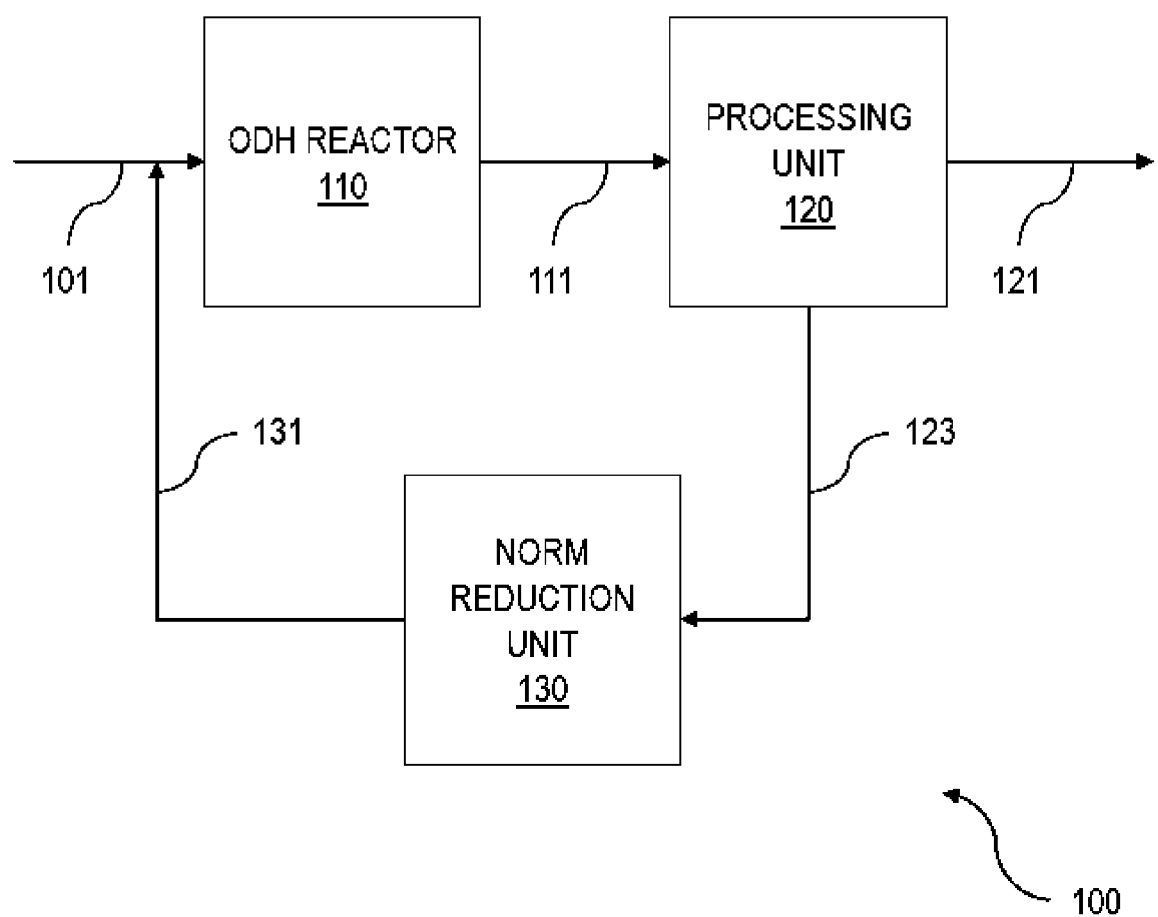
FIG. 1A is a schematic diagram of an example system for oxidative dehydrogenation.

FIG. 1A shows a schematic diagram of an embodiment of a system 100 for mitigating NORM in an oxidative dehydrogenation process. The system 100 includes an oxidative dehydrogenation (ODH) reactor 110, a processing unit 120, and a NORM reduction unit 130. A feed stream 101 includes oxygen, a hydrocarbon, and NORM. For example, the feed stream 101 includes oxygen, ethane, and radon. In some embodiments, the feed stream 101 includes additional hydrocarbons. In some embodiments, the feed stream 101 includes a decay product of radon.

The feed stream 101 flows to the ODH reactor 110. In the ODH reactor 110, at least a portion of the hydrocarbon from the feed stream 101 reacts with the oxygen from the feed stream 101 to form a dehydrogenated hydrocarbon and water. For example, an alkane from the feed stream 101 reacts with the oxygen from the feed stream 101 within the ODH reactor 110 to form a corresponding alkene and water. For example, ethane from the feed stream 101 reacts with oxygen from the feed stream 101 within the ODH reactor 110 to form ethylene and water. An effluent stream 111 flows out of the ODH reactor 110. A catalyst can be included in the ODH reactor 110 to promote reaction of the hydrocarbon with the oxygen. The effluent stream 111 includes the dehydrogenated hydrocarbon and water formed within the ODH reactor 110. The effluent stream 111 includes the NORM and any unreacted hydrocarbon (that is, any remaining hydrocarbon that did not react within the ODH reactor 110) originating from the feed stream 101.

In some embodiments, the olefins produced using the ODH reactor 110, or any of the processes or complexes described herein, can be used to make various olefin derivatives. Olefin derivatives include, but are not limited to polyethylene, polypropylene, ethylene oxide, propylene oxide, polyethylene oxide, polypropylene oxide, vinyl acetate, vinyl chloride, acrylic esters (e.g. methyl methacrylate), thermoplastic elastomers, thermoplastic olefins and blends and combinations thereof.

In some embodiments, ethylene and optionally α-olefins are produced in the ODH reactor 110, or any of the processes or complexes described herein, and are used to make polyethylene. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

The ODH reaction may occur in the presence of an inert diluent, such as carbon dioxide, nitrogen, or steam, which can be added to ensure the mixture of oxygen and hydrocarbon is outside of flammability limits. Determination of whether a mixture is outside of the flammability limits, for the prescribed temperature and pressure, is within the knowledge of the skilled worker. An ODH reaction that occurs within the ODH reactor 110 may also produce, depending on the catalyst and the prevailing conditions within the ODH reactor 110, a variety of other products which may include carbon dioxide, carbon monoxide, and oxygenates. These products leave the ODH reactor 110 via the effluent stream 111.

The effluent stream 111 flows to the processing unit 120. The processing unit 120 is configured to process the effluent stream 111 to form a product stream 121 and a recycle stream 123. The product stream 121 includes the dehydrogenated hydrocarbon. For example, the product stream 121 includes ethylene. The recycle stream 123 includes the NORM and the unreacted hydrocarbon.

The recycle stream 123 flows to the NORM reduction unit 130. The NORM reduction unit 130 is configured to reduce an amount of the NORM in the recycle stream 123 to produce a NORM-reduced recycle stream 131. The NORM-reduced recycle stream 131 includes the unreacted hydrocarbon (for example, the unreacted ethane exiting the ODH reactor 110) and includes less NORM in comparison to the feed stream 101. In some embodiments, the amount of NORM (including any NORM decay products) remaining in the NORM-reduced recycle stream 131 is substantially zero, for example, below the detection limit for analytical test methods typically used to detect such compounds. The NORM-reduced recycle stream 131 is recycled to the ODH reactor 110.

Figure 1B:
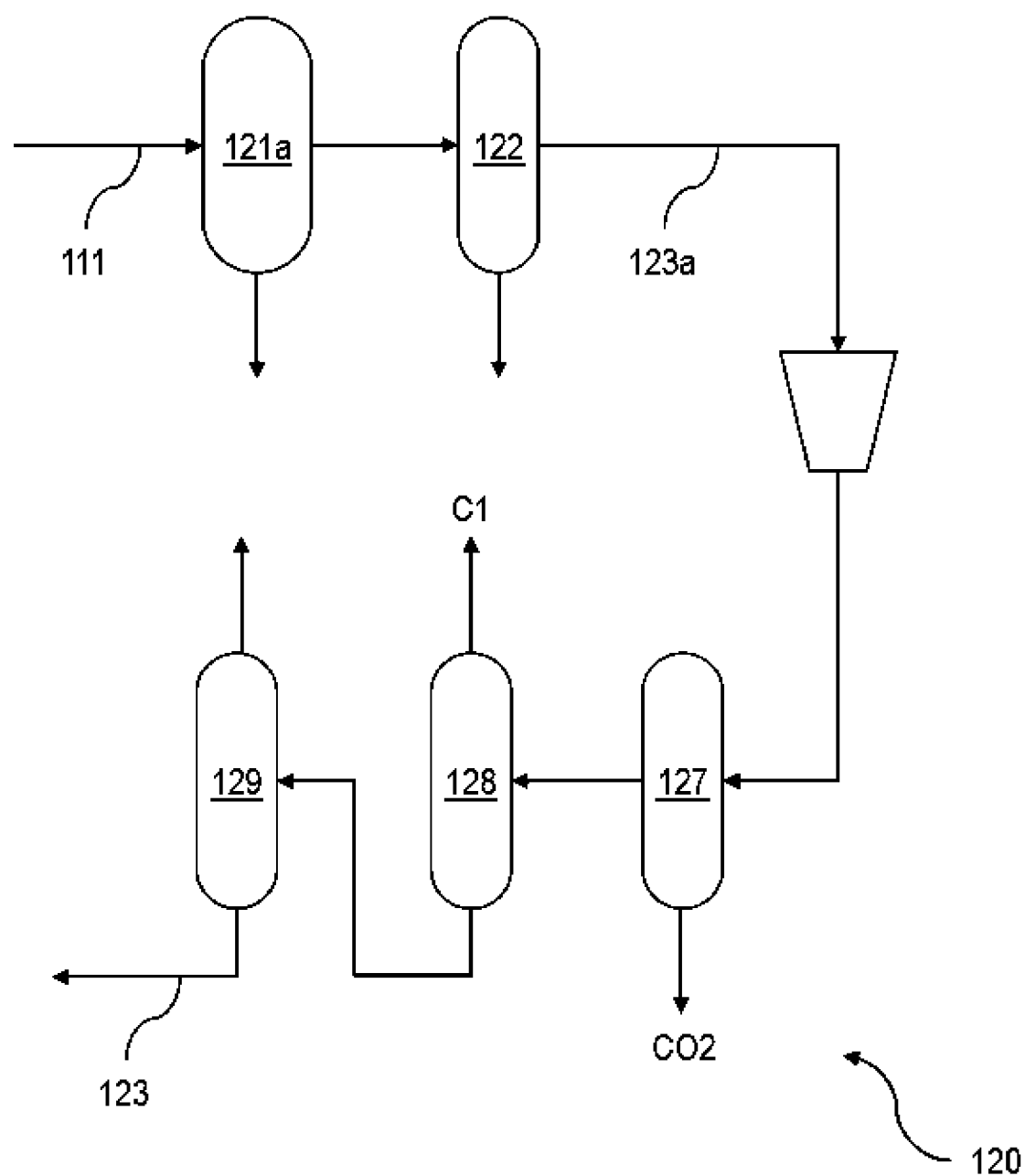
FIG. 1B is a schematic diagram of an example processing unit that can be implemented in the system of FIG. 1A.

FIG. 1B shows a schematic diagram of an embodiment of the processing unit 120, which can be implemented in system 100. The temperature of the effluent stream 111 in a typical ODH process can reach about 450° C. It can be desirable to lower the temperature of the effluent stream 111 before flowing to the processing unit 120. In some embodiments, a heat exchanger is included immediately downstream of the ODH reactor 110 to facilitate cooling.

In some embodiments, the effluent stream 111 (in some cases, pre-cooled) flows to the quench tower 121a to be cooled and condensed. This facilitates the removal of oxygenates, such as water and acetic acid. In some embodiments, the water and the acetic acid are flowed to an acetic acid separator, which separates the water from the acetic acid. In some embodiments, the water separated from the acetic acid in the acetic acid separator is treated, for example, in a bio-oxidation unit to remove any remaining carbon compounds. The treated water can then be fed, for example, to a cooling tower as makeup water.

In some embodiments, the gas from the quench tower 121a (with oxygenates removed) flows to the acetic acid scrubber 122. The acetic acid scrubber 122 can remove any remaining traces of acetic acid and other carbon compounds through oxidation and/or adsorption. Unconverted lower alkane (for example, ethane), corresponding alkene (for example, ethylene), unreacted oxygen, carbon dioxide, carbon monoxide, acetylene, inert diluent (for example, added to acetic acid scrubber 122), or any combination of these can exit the acetic acid scrubber 122 via stream 123a.

The oxygenates removed via the quench tower 121a and/or acetic acid scrubber 122 can include carboxylic acids (for example, acetic acid), aldehydes (for example, acetaldehyde) and ketones (for example, acetone). Because water is used in the acetic acid scrubber 122, in some embodiments, trace amounts of hydrocarbon may be dissolved in the water exiting the acetic acid scrubber 122. The amount of oxygenate compounds remaining in the stream 123a is substantially zero, for example, below the detection limit for analytical test methods typically used to detect such compounds. When oxygenates can be detected in the stream 123a, they may be present at a level of up to about 1 per million by volume (ppmv), in some cases up to about 5 ppmv, in other cases less than about 10 ppmv, in some instances up to about 50 ppmv and in other instances up to about 100 ppmv and can be present up to about 2 vol. %, in some cases up to about 1 vol. %, and in other cases up to about 1,000 ppmv.

The stream 123a is compressed (for example, in a single compressor or a series of compressors) and flows to an amine scrubber and/or a caustic wash tower 127. Any carbon dioxide present in the stream 123a is isolated by the amine scrubber and/or the caustic wash tower 127, and the carbon dioxide may be sold, recycled back to the ODH reactor 110, or both. The purified gas stream exiting the caustic wash tower 127 includes unconverted alkane (for example, ethane), corresponding alkene (for example, ethylene), and in some cases, inert diluent (for example, nitrogen). In some embodiments, the purified gas stream exiting the caustic wash tower 127 is compressed and dried to remove any remaining water. In some embodiments, after being compressed and dried, the purified gas stream is chilled before flowing to the demethanizer 128, in which C2/C2+ hydrocarbons are isolated and removed via bottoms. The remainder includes C1 hydrocarbons and remaining inert diluent and carbon monoxide (if any), which leaves the demethanizer 128 via overhead. The C2/C2+ hydrocarbon bottoms flows to the C2 splitter 129 which separates the stream into an ethylene product stream and an ethane feed stream. The ethane feed stream is the recycle stream 123 that flows to the NORM reduction unit 130. Radon, if present in the feed stream 101, follows ethane in the system 100 and is therefore also present in the recycle stream 123.

Figure 1C:
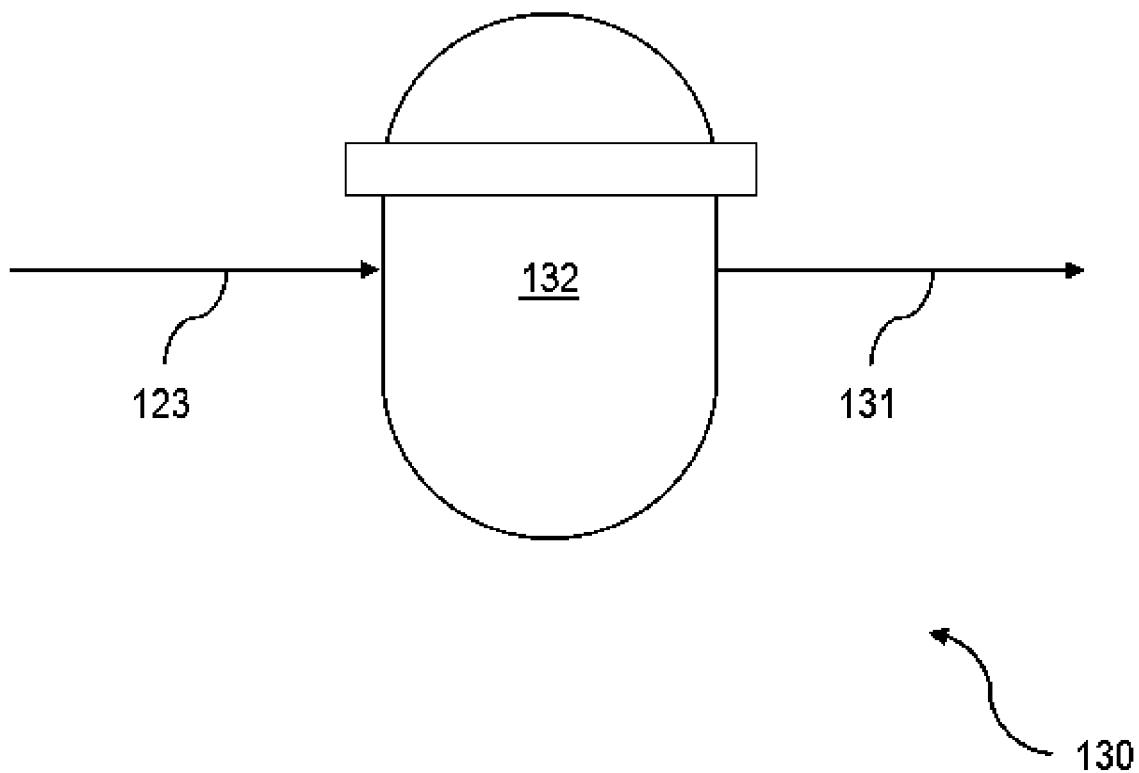
FIG. 1C is a schematic diagram of an example NORM (naturally occurring radioactive material) reduction unit that can be implemented in the system of FIG. 1A.

FIG. 1C shows a schematic diagram of an embodiment of the NORM reduction unit 130, which can be implemented in system 100. In some embodiments, the NORM reduction unit 130 includes an adsorption bed 132. The adsorption bed can include NORM adsorption material, such as activated carbon or zeolite, to capture radon, for example. In some implementations, the adsorption bed is impregnated with a metal, such as silver. The recycle stream 123 flows to the adsorption bed 132. The adsorption bed 132 captures NORM present in the recycle stream 123, and the NORM-reduced recycle stream 131 flows out of the adsorption bed 132. The NORM-reduced recycle stream 131, which comprises predominantly unconverted alkane (for example, ethane), is recycled to the ODH reactor 110. In some embodiments, the NORM-reduced recycle stream 131 is pre-treated before recycling to the ODH reactor 110. For example, the NORM-reduced recycle stream 131 is heated before recycling to the ODH reactor 110.

In some embodiments, the system 100 includes a second adsorption bed that is located upstream of the ODH reactor 110. The second adsorption bed can be substantially similar to the adsorption bed 132 described previously with respect to the NORM reduction unit 130. The feed stream 101 can flow to the second adsorption bed. The second adsorption bed can capture NORM present in the feed stream 101, and the feed stream 101 flowing out of the second adsorption bed can include less NORM in comparison to the feed stream 101 entering the second adsorption bed. In some embodiments, the feed stream 101 flowing out of the second adsorption bed is substantially free of NORM.

Figure 1D:
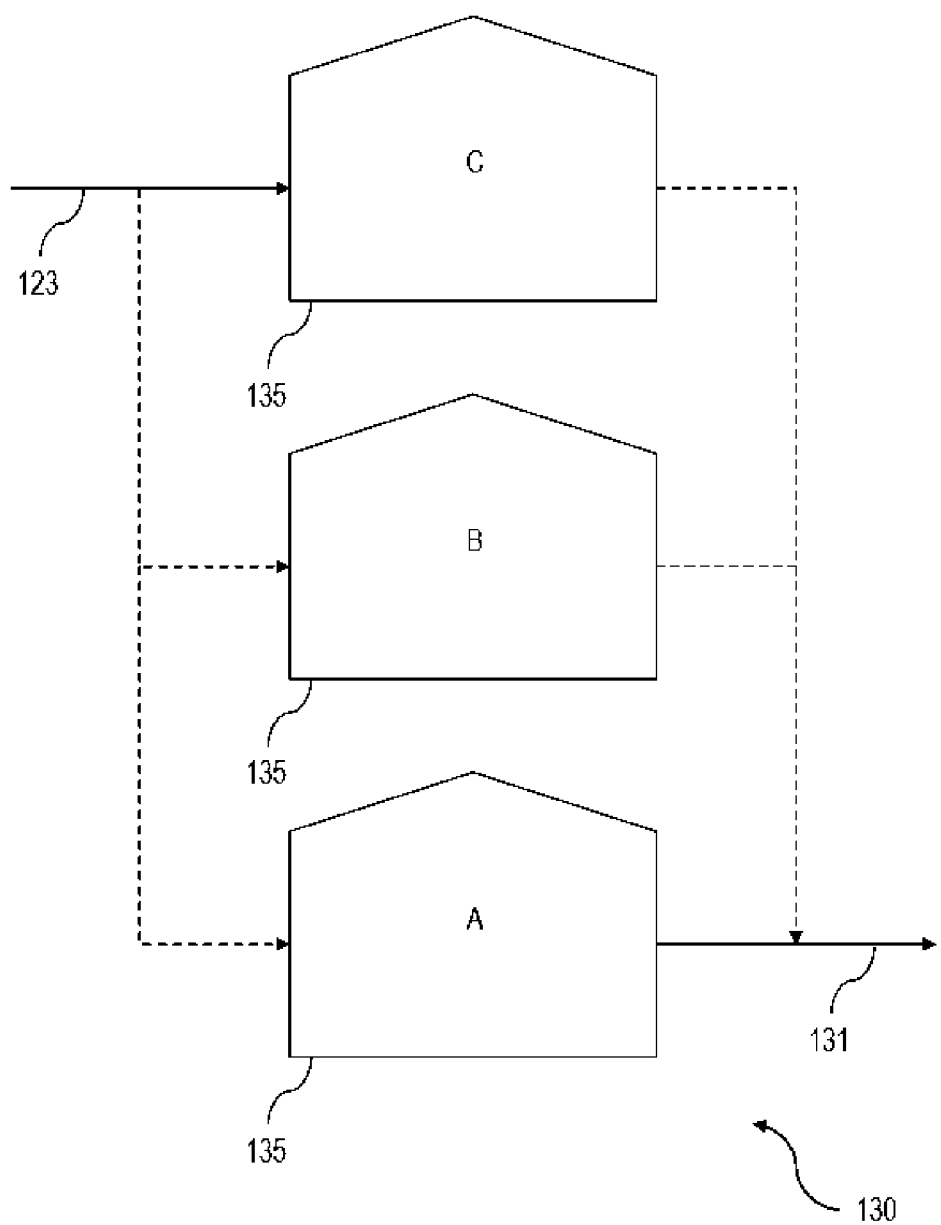
FIG. 1D is a schematic diagram of an example NORM reduction unit that can be implemented in the system of FIG. 1A.

FIG. 1D shows a schematic diagram of an embodiment of the NORM reduction unit 130, which can be implemented in system 100. In some embodiments, the NORM reduction unit 130 includes multiple storage tanks 135. In some embodiments, the storage tanks 135 are caverns, such as salt cavities. Although shown in FIG. 1D as having three storage tanks 135, the NORM reduction unit 130 can include fewer tanks (for example, two tanks) or more tanks (for example, four or five tanks, or more). The storage tanks 135 provide an inventorying process that allows the recycle stream 123 to be stored for a sufficient time that solid NORM decay products form. The solid NORM decay products (for example, lead-210, bismuth-210, polonium-210, or lead-206) can be filtered from the remaining, gaseous portion of the recycle stream 123. For example, a solids filter can be installed on each of the outlets of the storage tanks 135 to prevent solids from flowing out of the storage tanks 135. The remaining, gaseous portion of the recycle stream 123 is the NORM-reduced recycle stream 131 that is recycled to the ODH reactor 110.

In the instance shown in FIG. 1D, tank A has stored the recycle stream 123 for a sufficient time for solid NORM decay products to form, so tank A is supplying the NORM-reduced recycle stream 131 to the ODH reactor 110. Tank A can be considered the "feed tank" in this instance. Tank B is already filled with the recycle stream 123 and is storing the recycle stream 123 for enough time to form solid NORM decay products. Tank B can be considered the "wait tank" in this instance. Tank C is currently being filled with the recycle stream 123. Tank C can be considered the "fill tank" in this instance. The roles of Tanks A, B, and C can rotate, so that the process of system 100 can be continuous (as opposed to batch processing or semi-batch processing).

As mentioned previously, the NORM reduction unit 130 can include additional tanks. When enough solid NORM decay products have accumulated in any one of the tanks, that tank is either cleaned and re-used or disposed. The total number of tanks in the NORM reduction unit 130 can accommodate for such operation (that is, cleaning and/or disposing a tank) to occur without pulling the rest of the system 100 offline.

Figure 2:
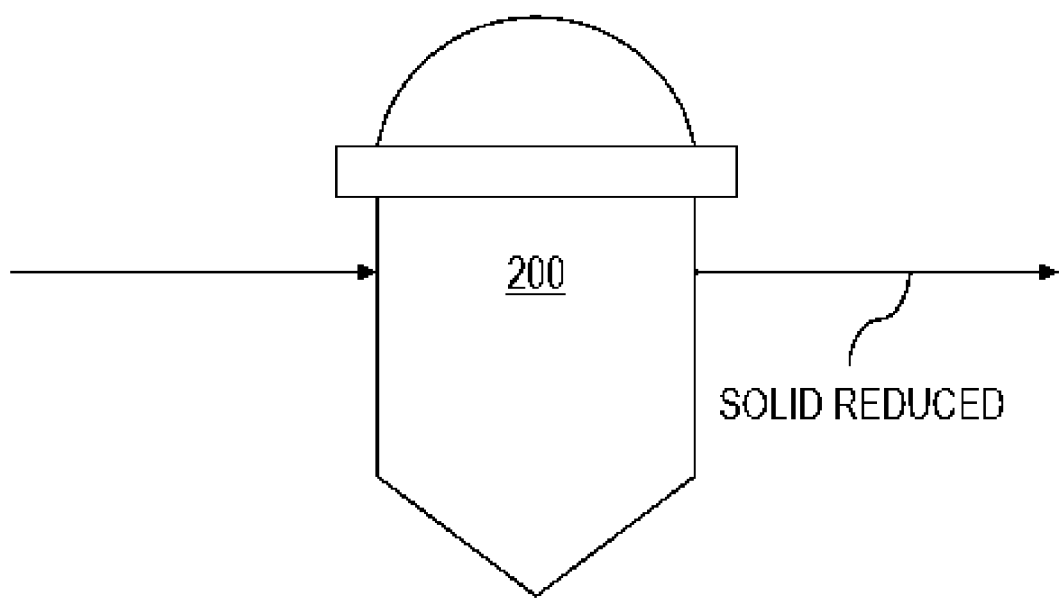
FIG. 2 is a schematic diagram of an example filter that can be implemented in the system of FIG. 1A.

FIG. 2 shows a schematic diagram of a filter 200, which can be implemented in the system 100. The filter 200 can include a bag filter to capture solid material. In some embodiments, the filter 200 includes a filter aid. A filter aid can be a finely divided material that can help control flow and remove solids. In some embodiments, the filter aid forms a porous layer on a septum (such as a screen or cloth that supports a filter cake) and becomes the filtering medium that traps solid material and prevents solid material from blinding the septum. An appropriate filter aid is light in weight and chemically inert, as filter aids facilitate mechanical filtration as opposed to chemical filtration. The filter aid can include, for example, dicalite diatomite, perlite, or cellulose particles.

In some embodiments, the filter 200 is included at each of the outlets of the storage tanks 135 of the NORM reduction unit 130. In such embodiments, the filter 200 prevents solid material from exiting the storage tanks 135. In some embodiments, the filter 200 is included upstream of the ODH reactor 110. In such embodiments, the filter 200 prevents solid material from entering the ODH reactor 110. For example, NORM flowing through the system 100 may decay into a solid NORM decay product. The filter 200 can capture such solid NORM decay products.

In some embodiments, a gas cyclonic separation device, which can separate solid material from a gas stream via vortex separation, is used in conjunction with or in place of the filter 200. The gas cyclonic separation device uses rotational effects and gravity to separate the solid material from the gas stream.

Figure 3:
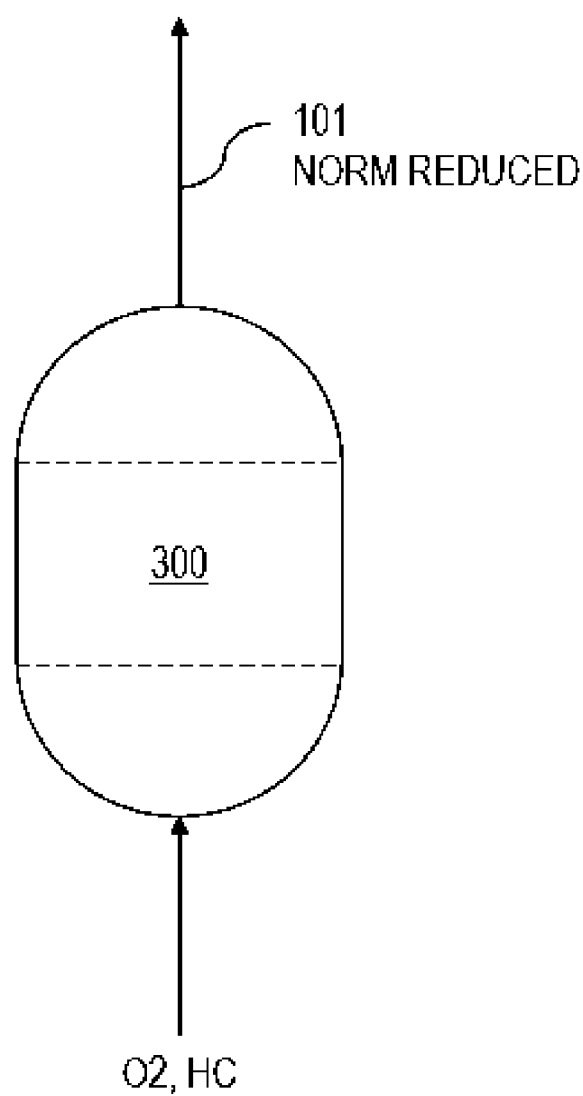
FIG. 3 is a schematic diagram of an example absorber that can be implemented in the system of FIG. 1A.

FIG. 3 shows a schematic diagram of an absorber 300, which can be implemented in the system 100. In some embodiments, a mixer may be used to mix a hydrocarbon containing gas with an oxygen containing gas in a flooded mixing vessel. In some embodiments, the system 100 includes the absorber 300 upstream of ODH reactor 110. Oxygen and hydrocarbon can feed directly into the absorber 300 to form a homogeneous mixture that includes oxygen and hydrocarbon to form the feed stream 101 that is flowed to the ODH reactor 110. In some embodiments, inert diluent is also fed to the absorber 300. In some embodiments, the absorber 300 includes an absorber bed that includes packing. In some embodiments, the absorber 300 is flooded with water. The absorber 300 can, for example, be in the form of a flooded gas mixing vessel. In essence, the gas feeding the absorber 300 bubbles through the flooded portion of the absorber 300. In some embodiments, the water flooding the absorber 300 includes an additive that interacts with NORM. For example, the additive can form a complex with radon. For example, the additive can precipitate NORM as a salt. In this way, any NORM-containing gas that bubbles through the flooded portion of the absorber 300 exits the absorber substantially NORM-reduced because the NORM remains in the flooded portion of the absorber 300.

The absorbent used in the absorber 300 can be chemical and/or physical in nature. Radon is more soluble in some organic solvents in comparison to water. As such, the absorber 300 can include an organic solvent for improving absorption of radon. The organic solvent can be, for example, decanoic acid or butanoic acid.

Figure 4A:
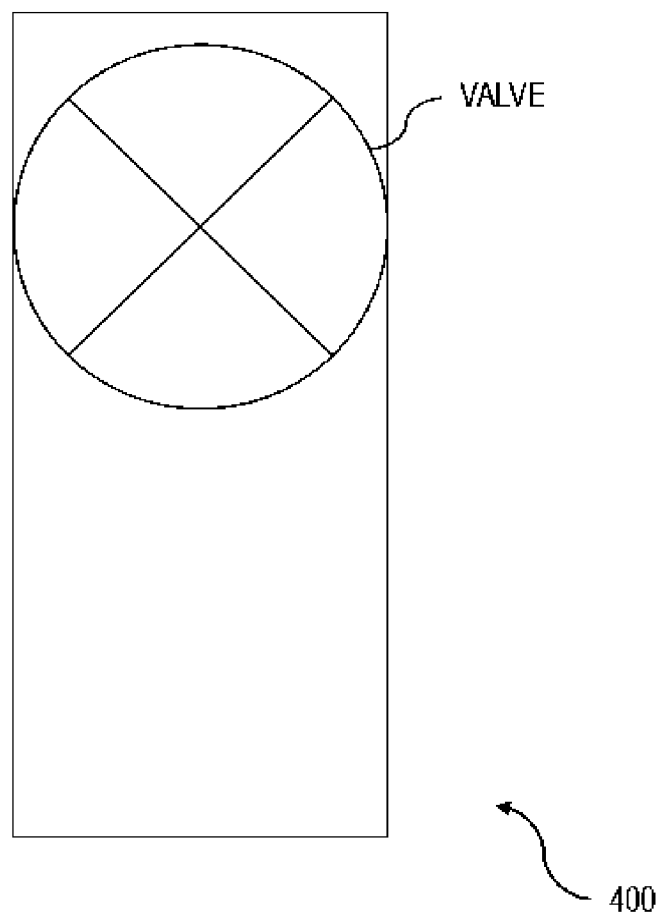
FIG. 4A is a schematic diagram of an example solid material receptacle that can be implemented in the system of FIG. 1A.

FIG. 4A shows a schematic diagram of a solid material receptacle 400, which can be implemented in the system 100. The solid material receptacle 400 is configured to accumulate solid material (for example, solid NORM decay products) that may be entrained in a flowing fluid (for example, a flowing gas). The solid material receptacle 400 can be installed in any portion of the system 100. Typically, the solid material receptacle 400 is installed on a lower portion of a pipe that is carrying fluid. Solid material will tend to flow in the lower portion of the pipe due to gravity, and the solid material receptacle 400 will capture and store such solid material.

Figure 4B:
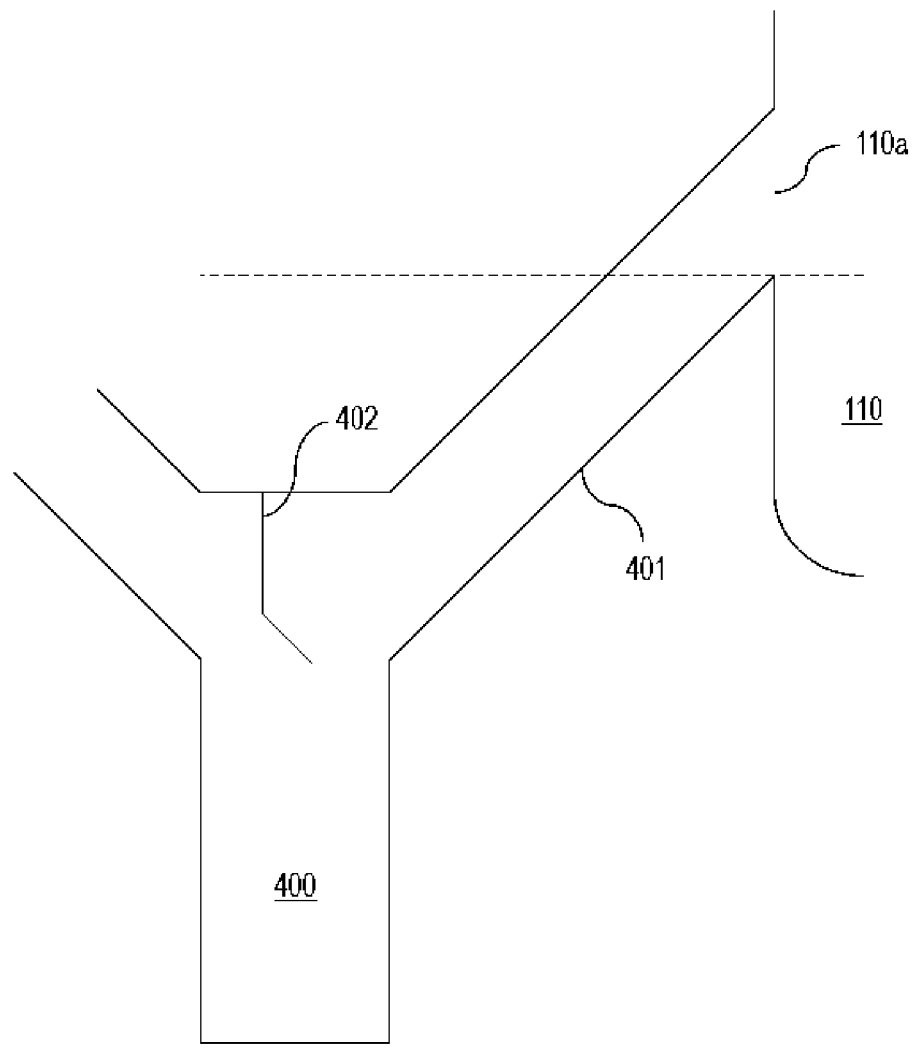
FIG. 4B is a schematic diagram of an example solid material receptacle that can be implemented in the system of FIG. 1A.

FIG. 4B shows a schematic diagram of an embodiment of the solid material receptacle 400. In some embodiments, the solid material receptacle 400 is positioned upstream of the ODH reactor 110, such that the solid material receptacle 400 accumulates solid material entrained in the fluid entering the ODH reactor 110. In some embodiments, the ODH reactor 110 defines an inlet opening 110*a* that is coupled to an inlet pipe 401. In some embodiments, a portion of the inlet pipe 401 is positioned below the inlet opening 110*a* with respect to gravity. In such embodiments, the solid material receptacle 400 is coupled to the portion of the inlet pipe 401 that is positioned below the inlet opening. In some embodiments, the inlet pipe 401 includes a baffle 402 that is configured to direct solid material to the solid material receptacle 400.

Figure 5:
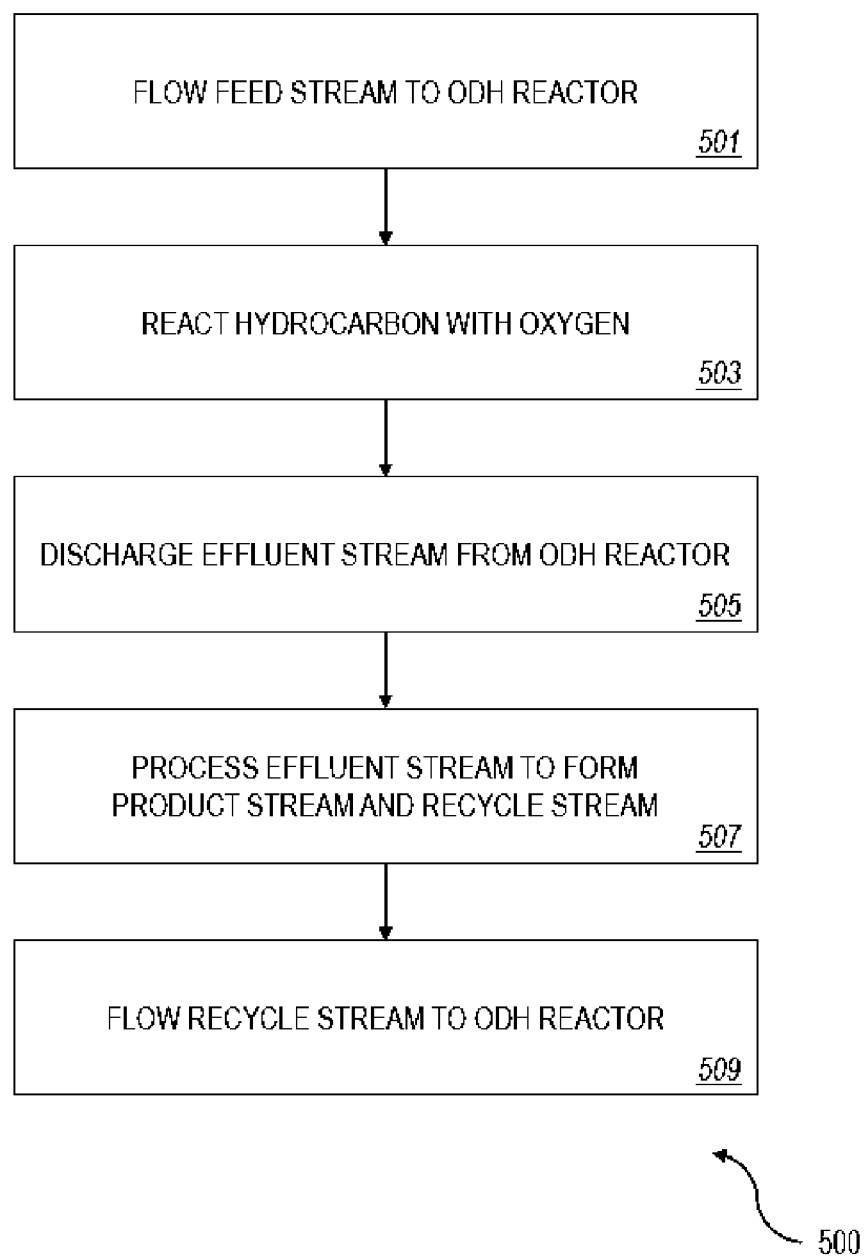
FIG. 5 is a flow chart of an example method for mitigating NORM in oxidative dehydrogenation.

FIG. 5 is a flow chart of an example method 500 for mitigating NORM in oxidative dehydrogenation. The method 500 can be, for example, implemented by the system 100. At block 501, a feed stream (for example, the feed stream 101) is flowed to an oxidative dehydrogenation reactor (for example, the ODH reactor 110). As mentioned previously, the feed stream 101 includes oxygen, hydrogen, and NORM. The feed stream 101 can optionally include additional components, such as an inert diluent.

At block 503, at least a portion of the hydrocarbon (for example, ethane) is reacted with the oxygen in the ODH reactor 110 to form dehydrogenated hydrocarbon (for example, ethylene) and water.

At block 505, an effluent stream (for example, the effluent stream 111) is discharged from the ODH reactor 110. As mentioned previously, the effluent stream 111 includes the dehydrogenated hydrocarbon (for example, ethylene), water, a remaining portion of the unreacted hydrocarbon (for example, unconverted ethane), and the NORM.

At block 507, the effluent stream 111 is processed, for example, in the processing unit 120 and the NORM reduction unit 130, to form a product stream and a recycle stream (for example, the NORM-reduced recycle stream 131). The product stream includes the dehydrogenated hydrocarbon (for example, ethylene). The NORM-reduced recycle stream 131 includes the remaining portion of the hydrocarbon (for example, ethane) and is substantially free of NORM.

In some embodiments, processing the effluent stream 111 at block 507 includes separating the remaining portion of the hydrocarbon from a remainder of the effluent stream 111 in the processing unit 120 to form an intermediate stream and flowing the intermediate stream through an adsorption bed (for example, the adsorption bed 132 of the NORM reduction unit 130).

In some embodiments, processing the effluent stream 111 at block 507 includes separating the remaining portion of the hydrocarbon from a remainder of the effluent stream 111 in the processing unit 120 to form an intermediate stream, storing the intermediate stream in a storage tank (for example, one of the storage tanks 135) for a sufficient time period such that the NORM decays into a solid material (for example, a solid NORM decay product), and filtering an outlet stream from the storage tank 135 to remove solid material from the outlet stream, thereby forming the NORM-reduced recycle stream 131.

At block 509, the NORM-reduced recycle stream 131 is flowed to the ODH reactor 110. In some embodiments, the feed stream 101 is flowed through an adsorption bed before flowing the feed stream 101 to the ODH reactor 110 at block 501. For example, the feed stream 101 is flowed through an adsorption bed that is substantially similar to the adsorption bed 132 described previously with respect to the NORM reduction unit 130. Flowing the feed stream 101 through the adsorption bed can cause NORM to be removed from the feed stream 101. In some embodiments, the feed stream 101 is filtered to remove solid material from the feed stream 101 before flowing the feed stream 101 to the ODH reactor 110.

The present disclosure also contemplates use of various tools commonly used for chemical reactors, including flowmeters, compressors, valves, and sensors for measuring parameters such as temperature, pressure and flow rates, all of which can be implemented in any of the previously described systems (for example, system 100). It is expected that the person of ordinary skill in the art would include these components as deemed necessary for safe operation.

Although shown as including one ODH reactor 110, the system 100 can include additional reactors. For example, the system 100 can include multiple ODH reactors 110. Although the concepts described herein are use with an ODH reactor, they may be used to decrease NORM in other reactor configurations. In some embodiments, the techniques are used to decrease NORM in selective oxidation reactor cycles or in steam cracking reactor cycles, among others. For example, the system 100 can include another reactor different from the ODH reactor 110, such as a selective oxidation reactor that reacts carbon monoxide with oxygen to form carbon dioxide. For example, the system 100 can include a selective oxidation reactor including a selective oxidation catalyst, such as silver-cerium (IV) oxide silica ($Ag-CeO_2/SiO_2$) or a copper/zinc/zirconium oxide ($CuZnZrO_x$).

While this specification contains many specific implementation details, these should not be construed as limitations on the scope of what may be claimed, but rather as descriptions of features that may be specific to particular embodiments. Certain features that are described in this specification in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an", or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described embodiments should not be understood as requiring such separation or integration in all embodiments, and it should be understood that the described components and systems can generally be integrated together or packaged into multiple products.

Accordingly, the previously described example embodiments do not define or constrain the present disclosure. Other changes, substitutions, and alterations are also possible without departing from the spirit and scope of the present disclosure.

Examples

The following examples are merely illustrative of the subject matter of this disclosure and are not intended to be limiting. Computational modeling of an oxidative dehydrogenation process with and without a NORM reduction unit was performed to demonstrate that the levels of radon present within the feed received by the oxidative dehydrogenation reactor will increase without mitigation using a reduction unit. The risk of radon levels continually increasing is the increase in radiation within the oxidative dehydrogenation reactor, the processing unit components, and associated connections, and also for the accumulation of decay products, such as lead 210, which can lead to reactor tube damage over time.

The modeling simulation was developed using Aspen Plus® V11 and included an oxidative dehydrogenation reactor, a processing unit (comprising a quench tower, amine scrubber, demethanizer, and C2 splitter), and a storage tank. Stoichiometry constants were generated using experimental results for an oxidative dehydrogenation process performed on a lab scale oxidative dehydrogenation reactor. Radon levels were modeled considering a half-life of radon of 91.68 hours (3.82 days). The simulated process used a feed comprising 80 mol % of ethane and 20 mol % of oxygen, with the results shown in Table 1 indicating the amount of radon in the feed during steady state operations. The ethane feed added to the oxidative dehydrogenation reactor in all cases was a mixture of fresh feed ethane and recycle ethane, and was modeled to be approximately 100,000 kg/hour. The ethane feed was optimized by using the fresh feed ethane to top up the ethane from the recycle feed to reach the required 100,000 kg/hr. The amount of recycle ethane used relative to fresh feed ethane was always greater and is a function of the conversion rate. The amount of radon in the fresh feed ethane was assumed to be constant in all cases of approximately 21.8 ppmw of radon. Table 1 shows the temperatures used for the oxidative dehydrogenation reaction, the conversion for ethane, and the time the recycle stream was held within the storage tank.

TABLE 1

Radon Feed Levels Simulation

| Case | Temp (° C.) | Conversion (%) | Storage Time (hours) | Steady State Radon in Ethane Feed (Fresh + Recycle) (ppmw) | Steady State Radon (kg/hour) in Ethane Feed Relative to Radon (kg/hour) in Fresh Ethane Feed (%) |
|---|---|---|---|---|---|
| 1 | 360 | 30.0 | 47.2 | 21.8 | 333.2 |
| 2 | 370 | 42.3 | 72.8 | 21.8 | 236.3 |
| 3 | 370 | 42.3 | 91.7 | 18.5 | 200.0 |
| 4 | 370 | 42.3 | 0.0 | 1507.7 | 16360.9 |

The results clearly show that without any NORM reduction the amount of radon in the feed would increase to levels over 1500 ppmw (see case 4), which is around 16,360% higher than the levels of radon found in the fresh feed. All three cases with NORM reduction using the storage tank show steady state radon levels (ppmv) that are similar to or even lower than that found in the fresh feed ethane.

The results also show that at lower conversions the storage time requirements are lower. This is due to the higher concentration of ethane found in the recycle stream, the ethane diluting the amount of radon present in the recycle stream. Increasing the conversion of ethane, by increasing the reaction temperature for example, would increase the recommended storage time to maintain a lower level of radon in the recycle feed, and ultimately in the feed received by the oxidative dehydrogenation reactor.

In the absence of a ethane recycle stream the amount of radon in the feed would stay constant at or near the levels found in commercially available ethane. However, without the use of an ethane recycle stream the commercial viability of the oxidative dehydrogenation process would be compromised as, depending on the conversion rate of ethane, significant amounts of ethane would be discarded.

INDUSTRIAL APPLICABILITY

The present disclosure relates to a system for mitigating naturally occurring radioactive materials in an oxidative dehydrogenation process.

The invention claimed is:
1. A system, comprising:
an oxidative dehydrogenation reactor configured to: i) receive a feed stream comprising oxygen, a hydrocarbon, and a naturally occurring radioactive material (NORM); and ii) react at least a portion of the hydrocarbon with the oxygen to form a dehydrogenated hydrocarbon and water, an outlet of the oxidative dehydrogenation reactor configured to provide an effluent stream comprising the dehydrogenated hydrocarbon, water, a remaining unreacted portion of the hydrocarbon, and the NORM;
a processing unit configured to: i) receive the effluent stream; and ii) process the effluent stream so that an outlet of the processing unit is configured to provide: i) a product stream comprising the dehydrogenated hydrocarbon; and ii) a recycle stream comprising the remaining unreacted portion of the hydrocarbon and the NORM; and
a NORM reduction unit configured to receive the recycle stream and reduce an amount of the NORM in the recycle stream so that an outlet of the NORM reduction unit is configured to provide a NORM-reduced recycle stream,
wherein the outlet of the NORM reduction unit is fluidically coupled with an inlet of the oxidative dehydrogenation reactor.

2. The system of claim 1, further comprising an adsorption bed positioned between the outlet of the NORM reduction unit and the inlet of the oxidative dehydrogenation reactor, wherein the adsorption bed is configured to remove NORM from any fluid entering the oxidative dehydrogenation reactor.

3. The system of claim 1, further comprising a filter upstream of the oxidative dehydrogenation reactor, the filter configured to capture and prevent solid material from entering the oxidative dehydrogenation reactor.

4. The system of claim 1, further comprising an absorber upstream of the oxidative dehydrogenation reactor, the absorber configured to remove NORM from the feed stream before the feed stream enters the oxidative dehydrogenation reactor.

5. The system of claim 1, further comprising a solid material receptacle upstream of the oxidative dehydrogenation reactor, the solid material receptacle configured to remove solid material entrained in a fluid before the fluid enters the oxidative dehydrogenation reactor.

6. The system of claim 5, further comprising an inlet pipe, wherein:
the oxidative dehydrogenation reactor defines an inlet opening coupled to the inlet pipe;
a portion of the inlet pipe is positioned below the inlet opening with respect to gravity; and
the solid material receptacle is coupled to the portion of the inlet pipe that is positioned below the inlet opening.

7. The system of claim 6, wherein the inlet pipe comprises a baffle configured to direct the solid material to the solid material receptacle.

8. A system, comprising:
an oxidative dehydrogenation reactor configured to: i) receive a feed stream comprising oxygen, a hydrocarbon and naturally occurring radioactive material (NORM); and ii) react at least a portion of the hydrocarbon with the oxygen to form a dehydrogenated hydrocarbon and water, an outlet of the oxidative dehydrogenation reactor configured to provide an effluent stream comprising the dehydrogenated hydrocarbon, water, a remaining unreacted portion of the hydrocarbon, and the NORM;
a processing unit configured to: i) receive the effluent stream; and ii) process the effluent stream so that an outlet of the processing unit is configured to provide: i) a product stream comprising the dehydrogenated hydrocarbon; and ii) a recycle stream comprising the remaining unreacted portion of the hydrocarbon and the NORM; and
a storage tank configured to store the recycle stream for a sufficient time period such that the NORM decays into a solid material, the storage tank fluidically coupled to the oxidative dehydrogenation reactor to recycle the remaining unreacted portion of the hydrocarbon from the recycle stream to the oxidative dehydrogenation reactor while the solid material remains within the storage tank.

9. The system of claim 8, wherein the storage tank comprises an outlet configured to discharge the remaining unreacted portion of the hydrocarbon from the recycle stream, and the outlet comprises a filter configured to capture and prevent solid material from exiting the storage tank.

10. The system of claim 9, further comprising an adsorption bed upstream of the oxidative dehydrogenation reactor, the adsorption bed configured to remove NORM from any fluid entering the oxidative dehydrogenation reactor.

11. The system of claim 9, further comprising a second filter upstream of the oxidative dehydrogenation reactor, the second filter configured to capture and prevent solid material from entering the oxidative dehydrogenation reactor.

12. The system of claim 9, further comprising an absorber upstream of the oxidative dehydrogenation reactor, the absorber configured to remove NORM from the feed stream before the feed stream enters the oxidative dehydrogenation reactor.

13. The system of claim 9, further comprising a solid material receptacle upstream of the oxidative dehydrogenation reactor, the solid material receptacle configured to remove solid material entrained in a fluid before the fluid enters the oxidative dehydrogenation reactor.

14. The system of claim 13, further comprising an inlet pipe, wherein:
the oxidative dehydrogenation reactor defines an inlet opening coupled to the inlet pipe;
a portion of the inlet pipe is positioned below the inlet opening with respect to gravity; and
the solid material receptacle is coupled to the portion of the inlet pipe that is positioned below the inlet opening.

15. The system of claim 14, wherein the inlet pipe comprises a baffle configured to direct the solid material to the solid material receptacle.

16. A method, comprising:
flowing a feed stream to an oxidative dehydrogenation reactor, the feed stream comprising oxygen, a hydrocarbon, and a naturally occurring radioactive material (NORM);
reacting at least a portion of the hydrocarbon with the oxygen in the oxidative dehydrogenation reactor to form a dehydrogenated hydrocarbon and water;
discharging an effluent stream from the oxidative dehydrogenation reactor, the effluent stream comprising the dehydrogenated hydrocarbon, water, a remaining unreacted portion of the hydrocarbon, and the NORM;
processing the effluent stream to form a product stream and a recycle stream, the product stream comprising the dehydrogenated hydrocarbon, the recycle stream comprising the remaining unreacted portion of the hydrocarbon with less NORM than the feed stream; and
flowing the recycle stream to the oxidative dehydrogenation reactor.

17. The method of claim 16, wherein processing the effluent stream comprises:
separating the remaining unreacted portion of the hydrocarbon from a remainder of the effluent stream to form an intermediate stream; and
flowing the intermediate stream through an adsorption bed, wherein the adsorption bed removes NORM from the intermediate stream to form the recycle stream.

18. The method of claim 16, further comprising flowing a first stream through an adsorption bed to provide the effluent stream, wherein the adsorption bed removes NORM from the first stream.

19. The method of claim 16, wherein processing the effluent stream comprises:
separating the remaining unreacted portion of the hydrocarbon from a remainder of the effluent stream to form an intermediate stream;
storing the intermediate stream in a storage tank for a sufficient time period such that the NORM decays into a solid material; and
filtering an outlet stream from the storage tank to remove solid material from the outlet stream, thereby forming the recycle stream.

20. The method of claim 19, further comprising filtering a first feed stream to remove solid material from the first feed stream to provide the feed stream.

* * * * *